(12) United States Patent
Stein et al.

(10) Patent No.: US 11,083,624 B2
(45) Date of Patent: Aug. 10, 2021

(54) MAGNETOELASTIC IMPLANTABLE ACTUATION DEVICE AND METHOD

(71) Applicant: The Regents of the University of Michigan, Ann Arbor, MI (US)

(72) Inventors: Joshua D. Stein, Ann Arbor, MI (US); Yogesh Gianchandani, Ann Arbor, MI (US); Venkatram Pepakayala, Chicago, IL (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 273 days.

(21) Appl. No.: 15/739,625

(22) PCT Filed: Jun. 24, 2016

(86) PCT No.: PCT/US2016/039398
§ 371 (c)(1),
(2) Date: Dec. 22, 2017

(87) PCT Pub. No.: WO2016/210351
PCT Pub. Date: Dec. 29, 2016

(65) Prior Publication Data
US 2018/0177638 A1 Jun. 28, 2018

Related U.S. Application Data

(60) Provisional application No. 62/184,585, filed on Jun. 25, 2015.

(51) Int. Cl.
*A61F 9/007* (2006.01)
*A61M 27/00* (2006.01)

(52) U.S. Cl.
CPC ....... *A61F 9/00781* (2013.01); *A61M 27/002* (2013.01); *A61F 2250/0013* (2013.01)

(58) Field of Classification Search
CPC .......... A61F 9/00781; A61F 2250/0013; A61F 9/0017; A61F 2009/00891; A61F 9/00745; A61M 27/002
See application file for complete search history.

(56) References Cited

U.S. PATENT DOCUMENTS

| 6,221,038 | B1* | 4/2001 | Brisken ............... A61B 17/2202 |
| | | | 604/22 |
| 8,702,639 | B2 | 4/2014 | Van Der Mooren et al. |
| 2002/0162582 | A1* | 11/2002 | Chu ........................ G02B 6/385 |
| | | | 134/105 |

(Continued)

OTHER PUBLICATIONS

Trierweiler et al. "Remotely activated, vibrational magnetoelastic array system for controlling cell adhesion" J. Biomedical Science and Engineering, vol. 6, Apr. 2013, pp. 478-482 (Year: 2013).*

(Continued)

*Primary Examiner* — Tatyana Zalukaeva
*Assistant Examiner* — Meagan Ngo
(74) *Attorney, Agent, or Firm* — Reising Ethington P.C.

(57) ABSTRACT

An implantable actuation device that may be used with a glaucoma drainage device or attached to an ocular surface, a method of making an implantable actuation device, and a method of preventing cell adhesion resulting from a glaucoma treatment procedure. The implantable actuation device is made from a magnetoelastic material. Actuation of the magnetoelastic material may help control cellular adhesion that may develop and undesirably disrupt proper healing when recovering from invasive surgical treatments. The implantable actuation devices may have small form factors and customized geometries which include three-dimensional curvatures to help promote the actuation of liquid flow and facilitate the removal of unwanted cells.

16 Claims, 14 Drawing Sheets

(56) References Cited

U.S. PATENT DOCUMENTS

| | | | |
|---|---|---|---|
| 2008/0097523 A1* | 4/2008 | Bolduc | A61B 17/064 606/219 |
| 2010/0042209 A1 | 2/2010 | Guarnieri | |
| 2010/0179375 A1* | 7/2010 | Andersson | H04R 25/606 600/25 |
| 2012/0088956 A1* | 4/2012 | Asnes | H04R 25/606 600/25 |
| 2012/0184892 A1 | 7/2012 | Bigler et al. | |
| 2013/0150775 A1* | 6/2013 | Dos Santos | A61F 9/00781 604/9 |
| 2013/0158464 A1* | 6/2013 | Samoocha | B08B 9/027 604/8 |
| 2015/0257930 A1* | 9/2015 | Lind | A61F 9/00781 604/9 |
| 2015/0257931 A1* | 9/2015 | Sanchez | A61F 9/00781 604/9 |

OTHER PUBLICATIONS

Kobayashi et al., 3D magnetic microactuator made of newly developed magnetically modified photocurable polymer and application to swimming micromachine and microscrewpump, Mar. 27, 2009, IEEE 22nd international conference on micro electro mechanical systems, pp. 11-14 (Year: 2009).*

Holmes et al. "Fabrication of Biocompatible, Vibrational Magnetoelastic Materials for Controlling Cellular Adhesion" Biosensors, vol. 2, Feb. 13, 2012, pp. 57-69.

Trierweiler et al. "Remotely activated, vibrational magnetoelastic array system for controlling cell adhesion" J. Biomedical Science and Engineering, vol. 6, Apr. 2013, pp. 478-482.

International Search Report for International application No. PCT/US2016/039398, dated Sep. 12, 2016, 4 pages.

Written Opinion for International application No. PCT/US2016/039398, dated Sep. 12, 2016, 7 pages.

\* cited by examiner

MAGNETOELASTIC IMPLANTABLE ACTUATION DEVICE AND METHOD

TECHNICAL FIELD

This invention relates generally to implantable actuation devices, and more particularly to small-scale actuation devices that are made from a magnetoelastic material and implanted to help control cellular adhesion.

BACKGROUND

Surgical implantation procedures as well as other invasive treatments often require the control or mitigation of cellular adhesion that may occur and undesirably disrupt proper healing. However, in the advent of more precise treatment methods that are typically less invasive, the scale to which cellular adhesion may occur is oftentimes smaller and more pinpointed as well. While chemical treatments to address undesirable cellular adhesion may help, treatments such as chemotherapeutic injections can lead to unwanted side effects. Using mechanical means to control cellular adhesion is a desirable option, but in view of the precise nature and smaller scale of treatments and surgical devices, it is necessary to form small-scale devices in complex geometrical shapes.

Ophthalmic procedures, such as glaucoma treatments, can pose particular challenges relating to controllable cellular adhesion. Glaucoma is the second leading cause of blindness globally, and is expected to afflict 79.6 million people by 2020. Glaucoma is commonly associated with high intraocular pressure (IOP), which is a result of increased resistance to the outflow of aqueous humor from inside the eye which can cause damage to the optic nerve and may result in an irreversible loss of vision. High IOP may be managed by pharmaceutical treatments or surgical interventions performed by laser or another surgical incision. Pharmaceutical treatments are typically administered as eye drops, whereas surgical methods include laser trabeculoplasty and, to a lesser extent, glaucoma filtration surgeries. Glaucoma drainage devices (GDDs) can be used for cases of intractable glaucoma, though findings from recent clinical trials have supported the use of GDDs much earlier in the disease course. As a result, utilization of GDDs has increased considerably in the past decade.

GDDs help to divert aqueous humor from the anterior chamber to an external reservoir. This external reservoir develops as a fibrous capsule, forming about 4 to 6 weeks after surgery, and helps to regulate flow of aqueous humor to the lymphatic system or nearby capillaries, thereby decreasing intraocular pressure (IOP). The size and permeability of the fibrous capsule is important, as a capsule that is too thick, for example, can lead to higher IOP, while a capsule that is too thin may lead to lower IOP or even hypotony. The primary determinants of IOP are capsular thickness and filtration surface area. The increase in the use of GDDs is likely related to a greater experience and appreciation for the efficacy of aqueous shunts, along with growing concerns about late complications associated with other filtering surgery techniques. GDDs are often reserved for patients with severe uncontrolled glaucoma, or where previous glaucoma surgeries have been unsuccessful. GDDs are also common as a primary procedure in patients with a high likelihood of trabeculectomy failure, including neovascular and uveitic glaucomas, and they can also be used in managing congenital and developmental glaucomas. GDDs may also be a primary surgical procedure for uncontrolled primary open-angle glaucoma. As mentioned above, chemical treatments to address undesirable cellular adhesion after implantation of a GDD may be used; however, the use of antifibrotic agents as adjuncts to drainage implant surgery has not proven effective in modulating capsular thickness. It should be noted that the control of fibrous capsule formation is important in other ophthalmic procedures as well, such as with treatments that form a bleb incision without a separate implantable device or other treatments that help facilitate fluid drainage.

Following various ophthalmic procedures, besides using chemical agents that may not always be effective, mechanical actuators may be used to assist in controlling fibrous capsule formation. Mechanical actuators such as magnetoelastic materials are promising because of their wireless transduction capability. However, fabrication of complex three-dimensional geometries and curvatures, which are typically necessary in ocular implants, particularly ocular implants that are adapted to the structure of a GDD, can be quite challenging when using magnetoelastic materials. For instance, passive sensors using magnetoelastic materials for detecting occlusion have been developed, but the geometry of these sensors has been limited to simple, single-axis curvatures.

SUMMARY

According to one embodiment, there is provided an implantable actuation device comprising an anchor adapted for fixedly mounting the implantable actuation device to a surface, an actuating paddle comprised of a magnetoelastic material, and a suspension component. The suspension component has a first end attached to the anchor and a second end attached to the actuating paddle. The suspension component allows for relative movement between the fixedly mounted anchor and the actuating paddle when the implantable actuation device is mounted to the surface.

According to another embodiment, there is provided an implantable ocular actuation device comprising a magnetoelastic membrane having a three-dimensional, non-spherically shaped profile.

According to another embodiment, there is provided a method of fabricating an implantable ocular actuation device. The method comprises the steps of patterning a magnetoelastic alloy membrane and annealing the membrane to shape it so that the membrane has a three-dimensional, non-spherically shaped profile.

According to another embodiment, there is provided a method of preventing cell adhesion resulting from a glaucoma treatment procedure. The method comprises the steps of anchoring a magnetoelastic paddle actuator to an ocular surface or a surface of a glaucoma drainage device and wirelessly applying a magnetic field to the magnetoelastic paddle actuator so that the paddle actuator vibrates and dispels at least some fibroblasts from the paddle actuator itself, the ocular surface, and/or the surface of the glaucoma drainage device.

BRIEF DESCRIPTION OF THE DRAWINGS

Preferred exemplary embodiments will hereinafter be described in conjunction with the appended drawings, wherein like designations denote like elements, and wherein.

DESCRIPTION OF THE ILLUSTRATED EMBODIMENTS

An implantable actuation device made from a magnetoelastic material may help control cellular adhesion that may occur and undesirably disrupt proper healing when recovering from particular invasive treatments. While the disclosure below is focused on ophthalmic procedures such as glaucoma treatments, the implantable actuation device may be applicable to procedures relating to other anatomical structures. The implantable actuation devices described herein may have a small form factor, customized geometries and three-dimensional curvatures for the actuation of liquid flow in order to prevent adhesion and facilitate the removal of cells such as fibroblasts that may be responsible for implant failure resulting from the development of a dense fibrous tissue encapsulation around the implant. Implantable actuation devices made at least partially from a magnetoelastic material may be remotely excited to resonance with a magnetic field generated by external coils, for example. Induced mechanical vibrations can work to limit cellular adhesion to a surface that may otherwise lead to implant encapsulation and subsequent failure. In a particular embodiment, the implantable actuation device is integrated with a glaucoma drainage device (GDD), which has the potential to greatly enhance the effectiveness of a GDD at lowering intraocular pressure (IOP).

Figure 1:
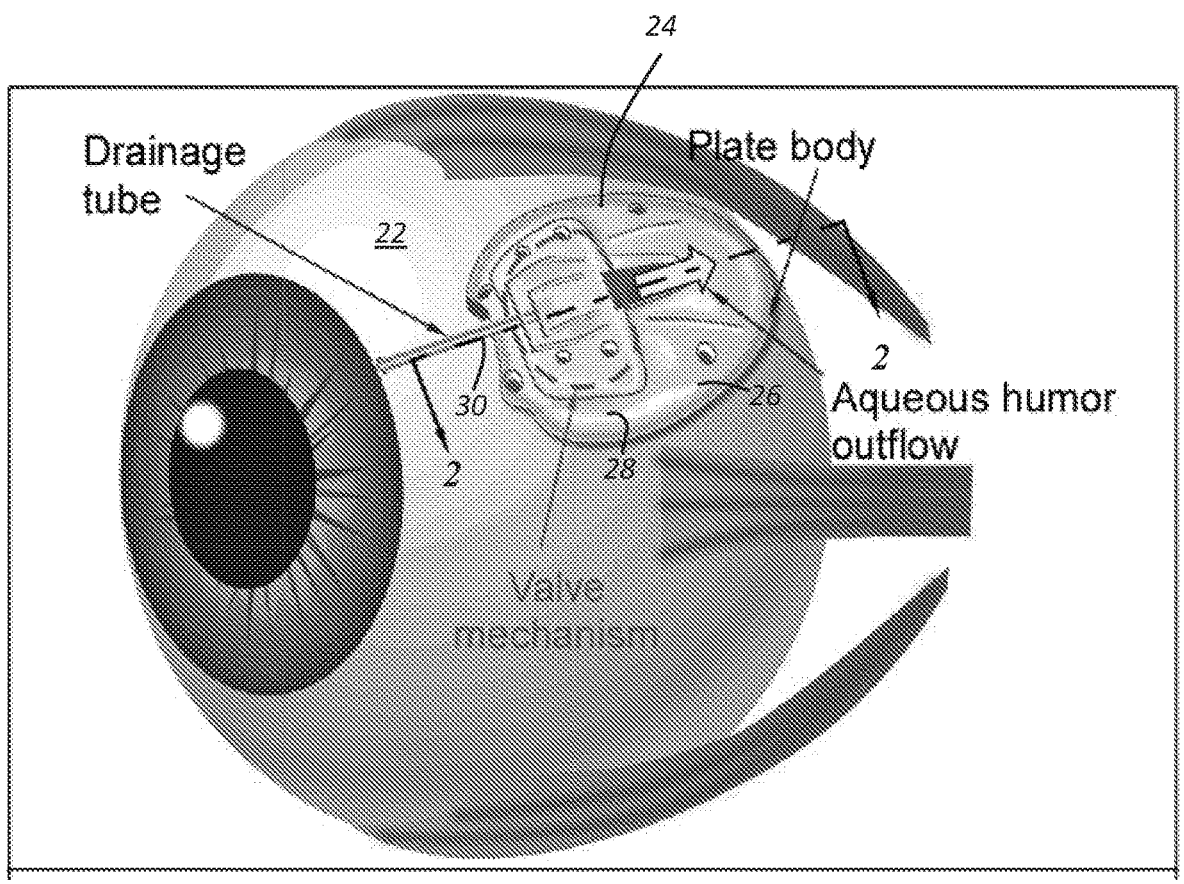
FIG. 1 is schematic perspective view of an eye without the conjunctiva depicted, showing one embodiment of a glaucoma drainage device (GDD)
Figure 2A:
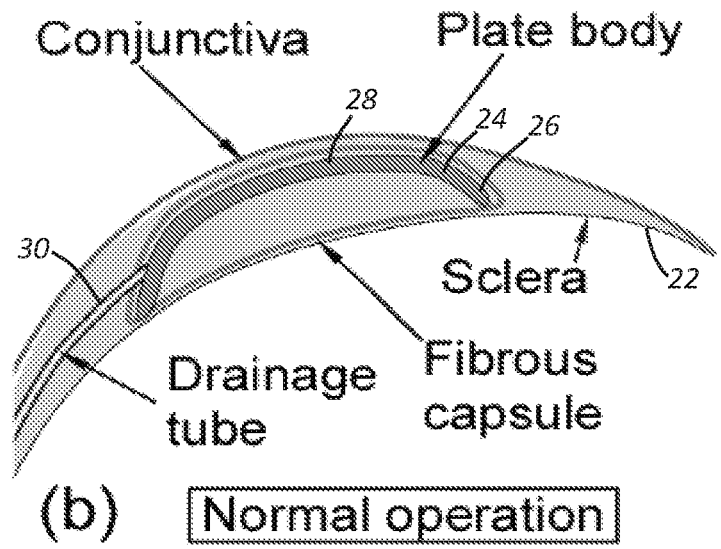
FIG. 2A is a cross sectional view taken along line 2-2 of FIG. 1 showing normal fibrous capsule formation.
Figure 2B:
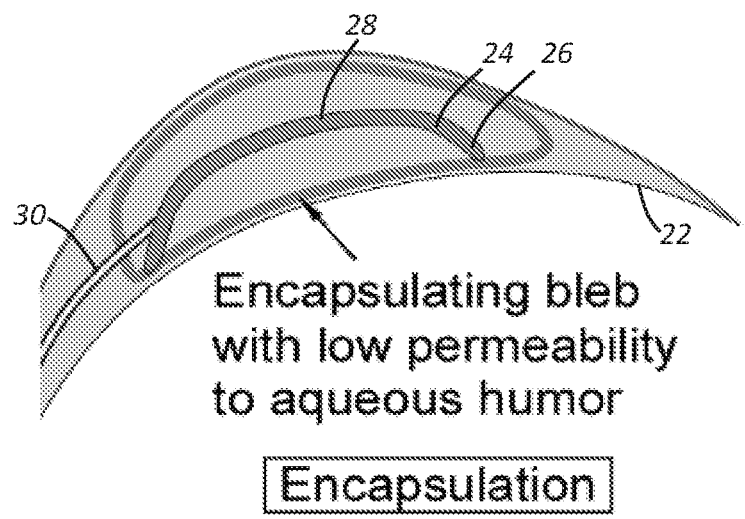
FIG. 2B is a cross sectional view taken along line 2-2 of FIG. 1 showing unwanted encapsulation that may form from excess cellular adhesion.
Figure 3A:
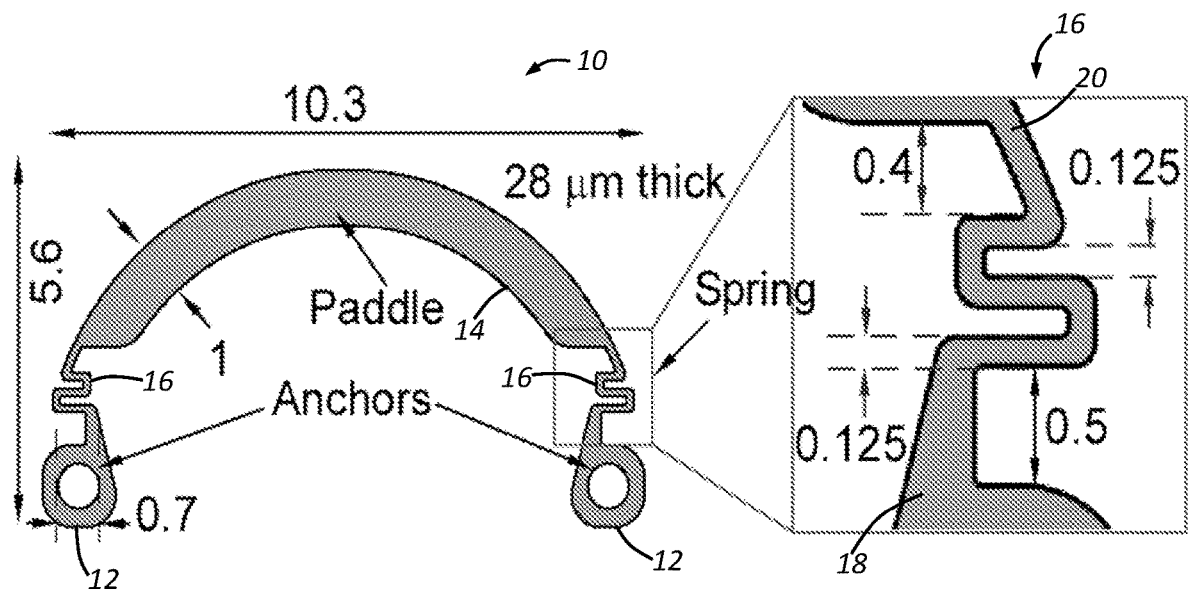
FIGS. 3A-3E show an implantable actuation device according to one embodiment.
Figure 3B:
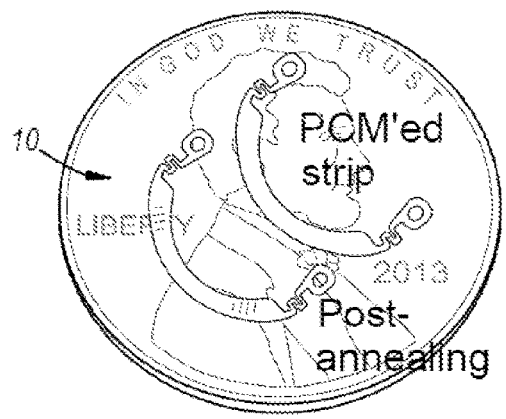
Figure 3C:
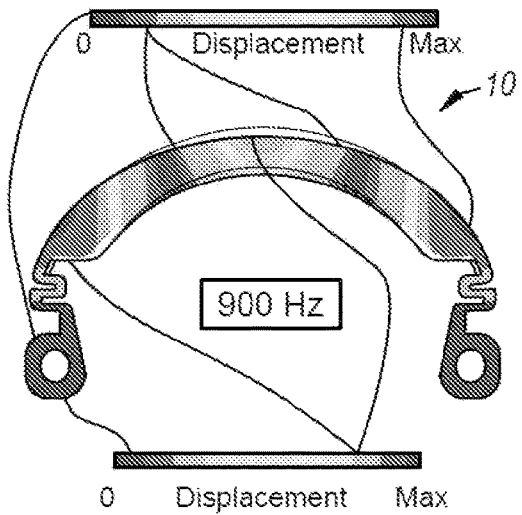
Figure 3D:
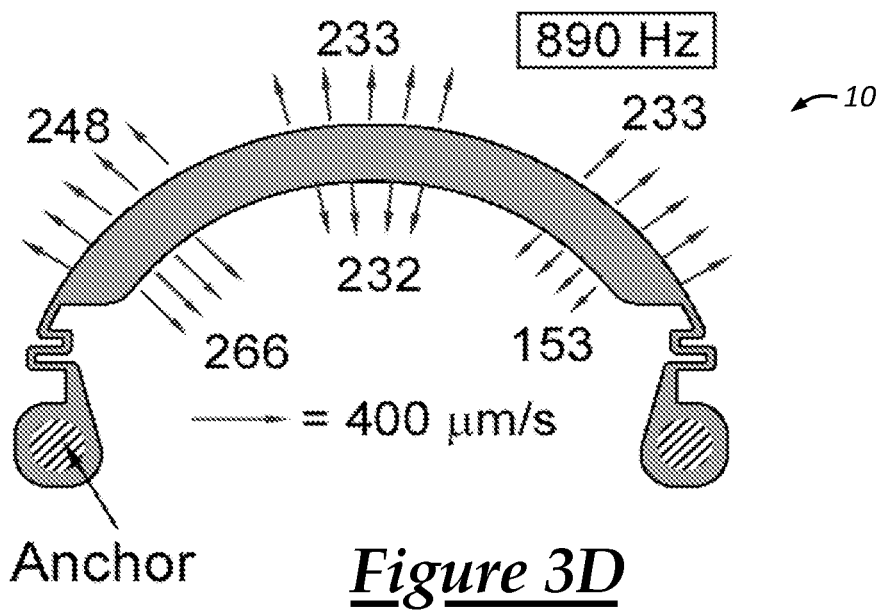
Figure 3E:
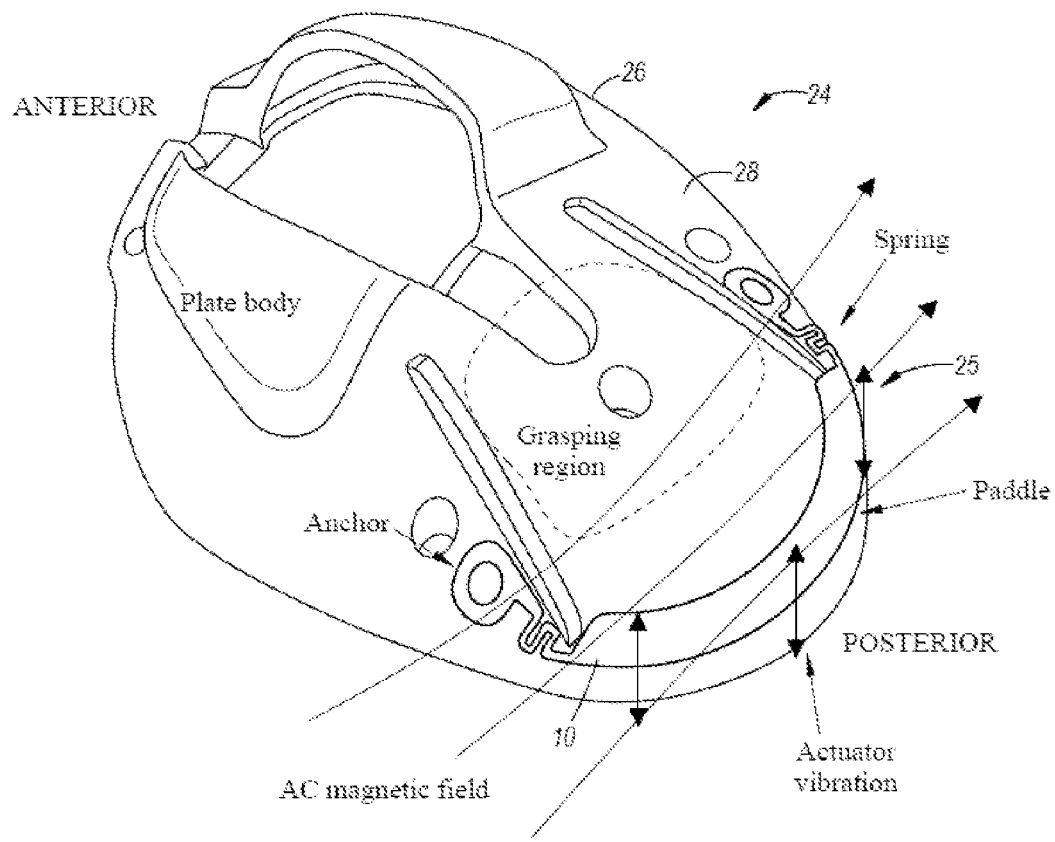

With reference to FIGS. 1-3E in general and FIGS. 3A-E in particular, there is illustrated an exemplary implantable actuation device 10, and more specifically, an implantable ocular actuation device. The implantable actuation device 10 may be comprised of a magnetoelastic thin film having a small form factor and a three-dimensional, non-spherically shaped profile. "Non-spherically shaped profile" as used herein means any geometric shape besides spheres, circular rings, and shapes with only a single-axis curvature. An example three-dimensional, non-spherically shaped profile 25 is shown in FIG. 3E. The implantable actuation device 10 includes one or more anchors 12, one or more actuating paddles 14 that are at least partially made of a magnetoelastic material, and one or more suspension components 16. Each suspension component 16 has a first end 18 attached to the anchor 12 and a second end 20 attached to the actuating paddle 14. The suspension component 16 allows for relative movement between the fixedly mounted anchor 12 and the actuating paddle 14 when the implantable actuation device is mounted to a surface, such as an ocular surface like the sclera 22 shown in FIGS. 1-2B. The suspension component may be implemented in any suitable form, such as a spring, an elastic or resilient member, etc. The actuating paddle may be any size or shape, depending on the desired anatomical mounting arrangement. The actuating paddle may also be perforated or otherwise formed in a way to help encourage vibratory motion and minimize damping. Similarly, the anchors may be of various sizes and shapes depending upon the usage environment of the implantable actuation device.

In a preferred embodiment, the implantable actuation device 10 is used with a GDD 24 situated on an ocular surface such as the sclera 22. The GDD 24 includes a body 26 having a surface 28. A drainage tube 30 extends from the body 26 of the GDD 24 to facilitate the drainage of aqueous humor from the eye, thereby alleviating undesirably high IOP. The illustrated GDD in FIGS. 1 and 3E is an Ahmed GDD that uses a drainage tube to permit flow of fluid out of the eye when IOP exceeds a threshold pressure; however, it should be noted that any operable type of GDD having any various shape may be used with an implantable actuation device. The drainage tube 30 of the GDD 24 drains aqueous humor into the space created by the body 26, which in this embodiment is plate-shaped and located in a subconjunctival space over the sclera 22. In FIG. 1, the conjunctiva is not shown for visibility.

Overtime, as illustrated in FIGS. 2A and 2B, a fibrous capsule of tissue or "bleb" is formed around the GDD serving as a reservoir for extra aqueous humor to drain from the eye. In a well-functioning implant with controlled IOP, the bleb has a thickness of less than 500 µm. This is schematically illustrated in FIG. 2A. However, as illustrated in FIG. 2B, in some patients, a thick, dense inner layer of collagen can form around the body, reducing permeability, which in turn, increases resistance to the outflow of aqueous humor. Certain patients, such as those more susceptible to scar tissue formation, may be more likely to develop unwanted cellular adhesion and encapsulation. For example, younger patients, patients with failed prior surgery or having combined surgeries, and African American patients may be more susceptible to scar tissue formation. The formation of the fibrous bleb is mediated by the adhesion and proliferation of fibroblasts and vascular endothelial cells on the implant surface 28. The extent of the fibrovascular tissue response can be correlated to the initial adhesion of these cells to the implant surface.

A magnetoelastic membrane may be used for the implantable actuation device 10 in order to vibrate and dispel at least some fibroblast cells from the paddle actuator 14 itself, the ocular surface 22, and/or the surface 28 of the GDD 24. Examples of suitable membranes include a foil, thin film, or any other operable sheet-like magnetoelastic form, whether as a multi-layer film or other structure (e.g., formed from material deposited on a substrate) or as a self-supporting structure (e.g., foil or a previously deposited layer removed from a substrate). In vitro studies have shown that local vibration, which may be produced by a magnetoelastic membrane, can influence the adhesion and proliferation of cells. Above certain oscillating stress limits, human fibroblast cells will fail to adhere to a substrate. Additionally, it has been shown through in vitro studies that vibrations can negatively influence the proliferation of certain types of mouse embryonic fibroblast cells. In one specific example, vibration amplitudes measuring approximately 100 nm, at frequencies of 100 Hz and 1 kHz were tested. In another example, a significant reduction in adhered fibroblast cell count resulted from vibration amplitudes of 150 nm, using planar rectangular magnetoelastic resonators operating at 176 kHz.

Magnetoelastic materials exhibit an elastic response to applied magnetic fields in an effect termed Joule magnetostriction. As a result, magnetoelastic structures can be excited to mechanical resonance using oscillating magnetic fields. An inverse effect, called the Villari effect describes the magnetization resulting from applied mechanical strain. In a vibrating structure, such as the implantable actuation device 10, the Villari effect can take place concurrently with Joule magnetostriction. The coupling between magnetization and mechanical stress or strain can be expressed by a pair of equations. For a one-dimensional system, equations (1) and (2) may be used:

$$\varepsilon = \frac{\partial \varepsilon}{\partial \sigma}\bigg|_H \sigma + \frac{\partial \varepsilon}{\partial H}\bigg|_\sigma H \quad (1)$$

$$B = \frac{\partial B}{\partial \sigma}\bigg|_H \sigma + \frac{\partial B}{\partial H}\bigg|_\sigma H \quad (2)$$

where σ is stress, ε is strain, B is magnetic flux density and H is magnetic field intensity (all small signal). The partial derivatives include:

$$\frac{\partial \varepsilon}{\partial \sigma}\bigg|_H$$

which is the compliance at constant H, $s^H$;

$$\frac{\partial B}{\partial H}\bigg|_\sigma$$

which is the permeability at constant stress, $\mu^\sigma$; and $$\frac{\partial \varepsilon}{\partial H}\bigg|_\sigma$$

and $$\frac{\partial B}{\partial \sigma}\bigg|_H$$

can both be represented by d, the magnetostrictive coefficient. The strength of vibration may be determined by the magnetostrictive coefficient, d, which can be dependent on DC bias conditions. For a maximum resonant response, which may be desirable in some embodiments, the DC magnetic field should bias the material where d is high.

As illustrated in FIGS. 3A-3E, an implantable actuation device 10 that is at least partially made of a magnetoelastic material can be integrated with a GDD 24 to limit cellular adhesion on the GDD surface 28 via the vibratory response of the magnetoelastic material. The actuation device 10 may be embedded within the GDD, or affixed to the GDD prior to surgical implantation. Post-implantation, the actuation device 10 may be deployed periodically—perhaps only for a few minutes per day depending on the desired treatment regimen—using a small external coil to generate an oscillating magnetic field, for example. The external coil may be positioned a few centimeters from the implant while a weak magnetic field is generated (e.g., less than 20 G). The external coil may be embedded in a toothbrush or a wearable device, for example. It would be safe for the procedure to be administered by the patient or a caregiver with minimal instructions. In one embodiment, an excitation signal may be used to measure feedback in order to monitor when and/or if the patient is properly administering an actuation regimen.

While magnetoelastic materials are typically attractive for use in wireless sensors and actuators, the fabrication of complex three-dimensional geometries and non-spherical surfaces can be a challenge. This is a predominant concern for implantable applications where such shapes should conform to biological features and/or implants like a GDD. In a preferred embodiment, the implantable actuation device hugs the GDD surface conformally in order to avoid changes to the manner in which the device fits the eye, as well as to prevent possible damage to the surrounding ocular tissue.

FIGS. 3A-3E illustrate one embodiment of an implantable actuation device 10. FIG. 3B shows a prototype actuator after photochemical machining (right) and after annealing (left). This embodiment includes an actuating paddle 14 that can circumscribe the posterior or downstream portion of the surface 28 of a plate body 26 of a GDD 24, such as that illustrated in FIG. 3E. The actuating paddle 14 extends between two anchors 12 and may be connected to the anchors via two suspension components 16. Each suspension component 16 includes a first end 18 attached to an anchor 12 and a second end 20 attached to the actuating paddle 16. The suspension components 16 in this embodiment are folded structures measuring approximately 125 μm wide, with the length of each suspension component measuring approximately 1.6×0.75 mm². The suspension components 16 relieve stress from the anchors 12, which in this embodiment, are fixedly mounted to the surface 28 of the GDD. Any operable fixation method may be used to affix the anchors to a surface, including an adhesive such as an epoxy adhesive, a mechanical fastener such as a rivet or post, or a suture if the anchors are mounted to a surface of an anatomical structure, to cite a few examples. The anchors in this particular embodiment are 1.3×1.3 mm², with a single perforation measuring 0.7 mm in diameter. The perforation is not required, and it should also be noted that for any of the embodiments described in this application, the size and shape of the various device components may be adapted based upon the desired implementation of the implantable actuation device and is not limited to the particular sizes and shapes disclosed herein.

FIG. 3C shows the resonant behavior of the implantable actuation device 10 according to this embodiment. FIG. 3C further illustrates the mode shapes showing the maximum vibration amplitudes. The resonant behavior was simulated in COMSOL Multiphysics 4.4. Coupled solid-mechanics and magnetic fields physics, which were approximated by equations (1) and (2) above, were used to simulate the behavior of magnetoelastic materials in an oscillating magnetic field. Mechanical and magnetic properties used in this simulation were derived from manufacturer data sheets among other sources. The amount of damping due to the liquid environment may be obtained experimentally using laser displacement meter measurements performed on fabricated actuation devices, as described in more detail below. The simulations predict multiple flexural modes for the implantable actuation device 10 depicted in FIG. 3C, with a frequency of 900 Hz showing maximum resonant amplitudes in this example.

Figure 9:
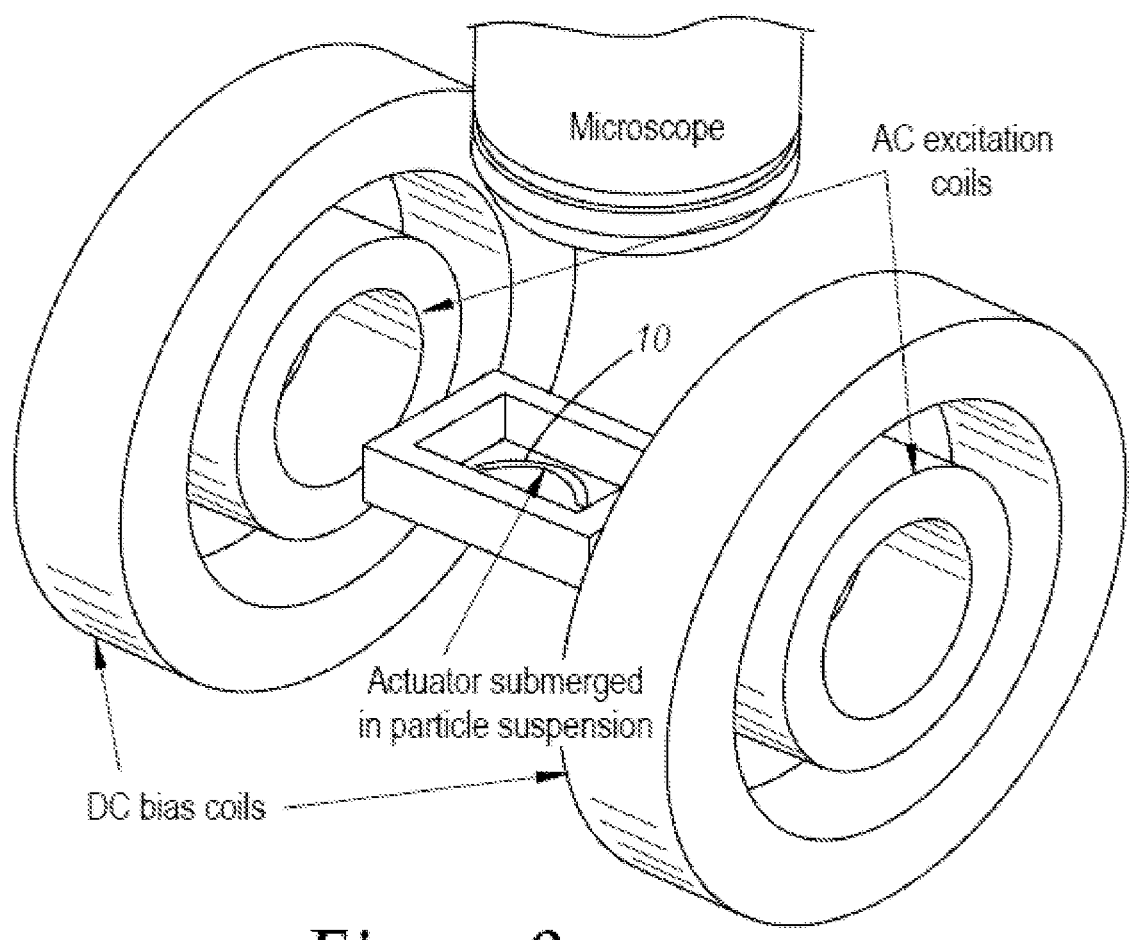
FIG. 9 is a schematic view of an example test set up for an implantable actuation device.
Figure 10:
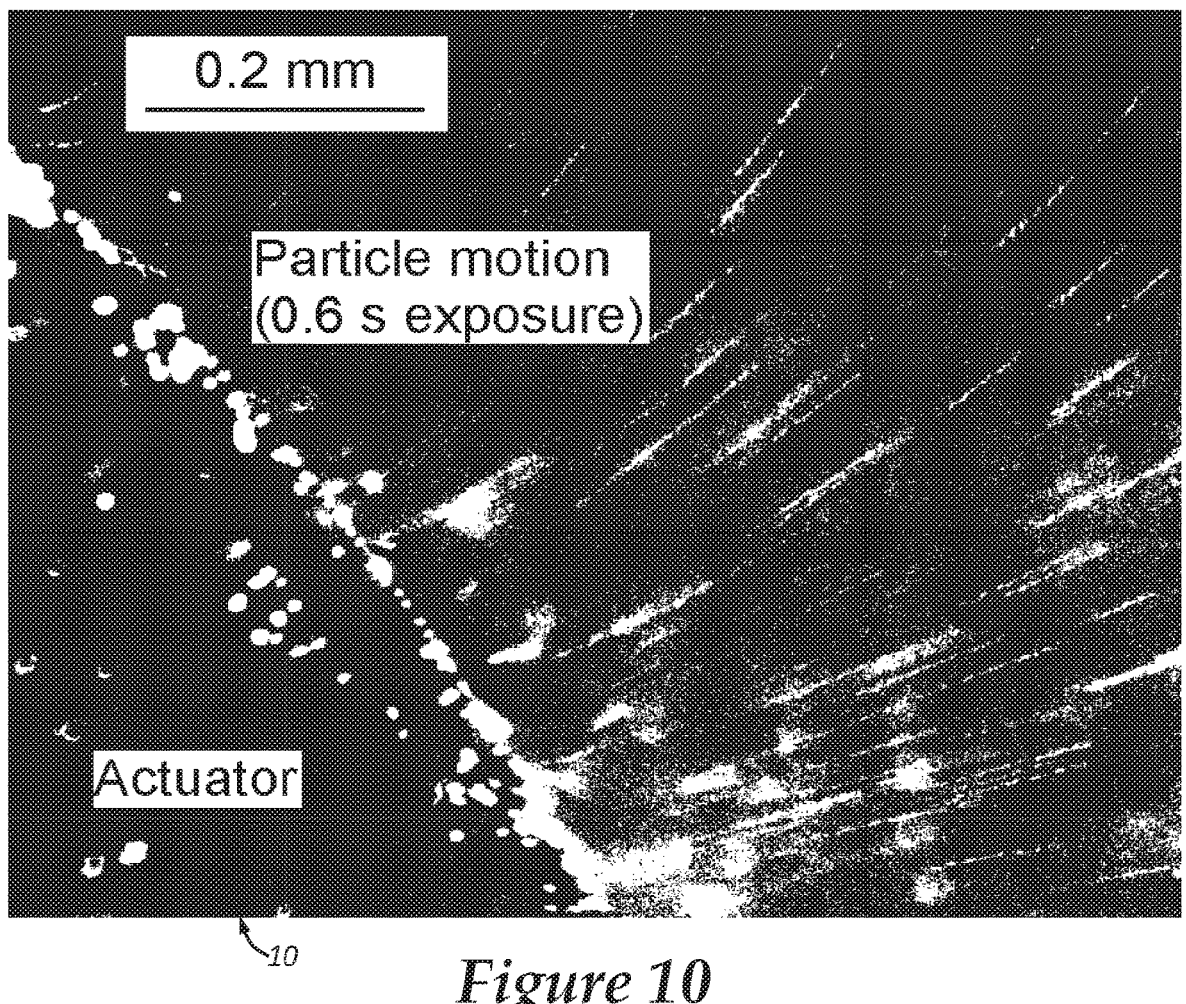
FIG. 10 is an image showing particle motion from an implantable actuation device.

FIG. 3D shows estimated particle velocities that were observed when the implantable actuation device 10 was experimentally evaluated using an optical approach to determine resonant modes that generate maximum fluid motion. The implantable actuation device 10 according to this embodiment, as well as the other illustrated embodiments describe below, were placed in an aqueous suspension of 3.1 μm diameter particles (Fluoro-Max dyed green aqueous fluorescent particles, Thermo Fisher Scientific Inc., Waltham, Mass.) at a concentration 6 ng/ml. These particles have an excitation wavelength of 468 nm and an emission wavelength of 508 nm. The motion of the particles was observed under a microscope (Olympus SZX12 stereo microscope, Olympus Corporation, Tokyo, Japan), and the images were recorded using a digital camera (Pentax K7, Ricoh Company, Ltd., Tokyo, Japan). The particle trajectories were captured using long exposure (e.g., 0.6 s) photographs taken through the microscope in this example. The particle velocities were estimated based on the distances travelled by the particles in the exposure time of the photographs. All measurements in this particular experimental set up were taken at 23° C. Magnetic biasing was provided by a set of Helmholtz coils that provided a DC magnetic field, and activated using a second set of coils, coaxial to the first, that transmitted an AC magnetic field, as illustrated in the exemplary test set up of FIG. 9. The DC biasing field in this particular embodiment measured 20 G, while the excitation AC magnetic field measured 4 G, rms. The frequency of the excitation AC magnetic field varied from 0.1-5 kHz. Each annealed actuation device was attached to the DMLS-fabricated test plate at the anchors using a cyanoacrylate adhesive. The coils generating the AC excitation magnetic field were located 25-30 mm away from the anchored actuator. An example long exposure photograph showing the streaks of particle motion is shown in FIG. 10, where image thresholding was used for better visibility. At this location in particular, the particles travelled an average distance of 149 μm in 0.6 s. The velocity of the particles is thus estimated to be about 248 μm/s. Returning to FIG. 3D, estimated particle velocities were observed and schematically represented. The regions of the implantable actuation device showing particle motion correspond to the antinodes of that particular resonant mode. The mode shapes indicated by the observed antinodes generally correspond to the simulated mode shapes shown in FIG. 3C. This embodiment has six regions where particle flow is generated, with an average flow velocity of 230 μm/s at a resonant frequency of 890 Hz. The flow pattern indicates the third flexural mode of the paddle, confirming the simulated mode shape. In a preferred embodiment, vibrational motion out of the plane of the implantable actuation device is preferred, which serves to "pump" the surrounding liquid, which is different than most magnetoelastic actuators which facilitate longitudinal vibrational motion. By selecting appropriate frequencies, out of plane vibrational motion can be facilitated, as skilled artisans will appreciate.

FIG. 3E illustrates the implantable actuation device 10 attached to the surface 28 of the body 26 of the GDD 24. More particularly, FIG. 3E is a model of an Ahmed GDD, created by using a Scanco μCT 100 micro-computed tomography (μCT) system. A software package (Materialise Mimics 14) can be used to create a 3D mesh from the scan data which can then be imported into CAD and FEA tools. Another software module (Materialise 3-Matic) can then be used to repair the mesh and remove any imperfections and artifacts caused by the scanning process. The design of the actuator can accommodate various features on the GDD 24. Three perforations in the posterior of the GDD allow the growth of fibrous tissue that "rivets" the body 26 of the GDD to the scleral surface 22 on which it may rest, whereas two in the anterior may be used to suture the implant in place. In addition, there are two ridges located in the posterior of the GDD. It may be beneficial if the actuator design avoids the perforations and ridges on the plate surface 28. Additionally, there may be considerations related to the handling of the GDD 24 during the implantation procedure. During the implantation procedure, the GDD may be grasped with forceps, typically from the posterior of the valve mechanism, and placed under the conjunctiva before it is sutured to the sclera. The implantable actuation device may be designed avoid the area of the plate body where forceps are typically positioned during surgical implantation procedures.

Figure 11A:
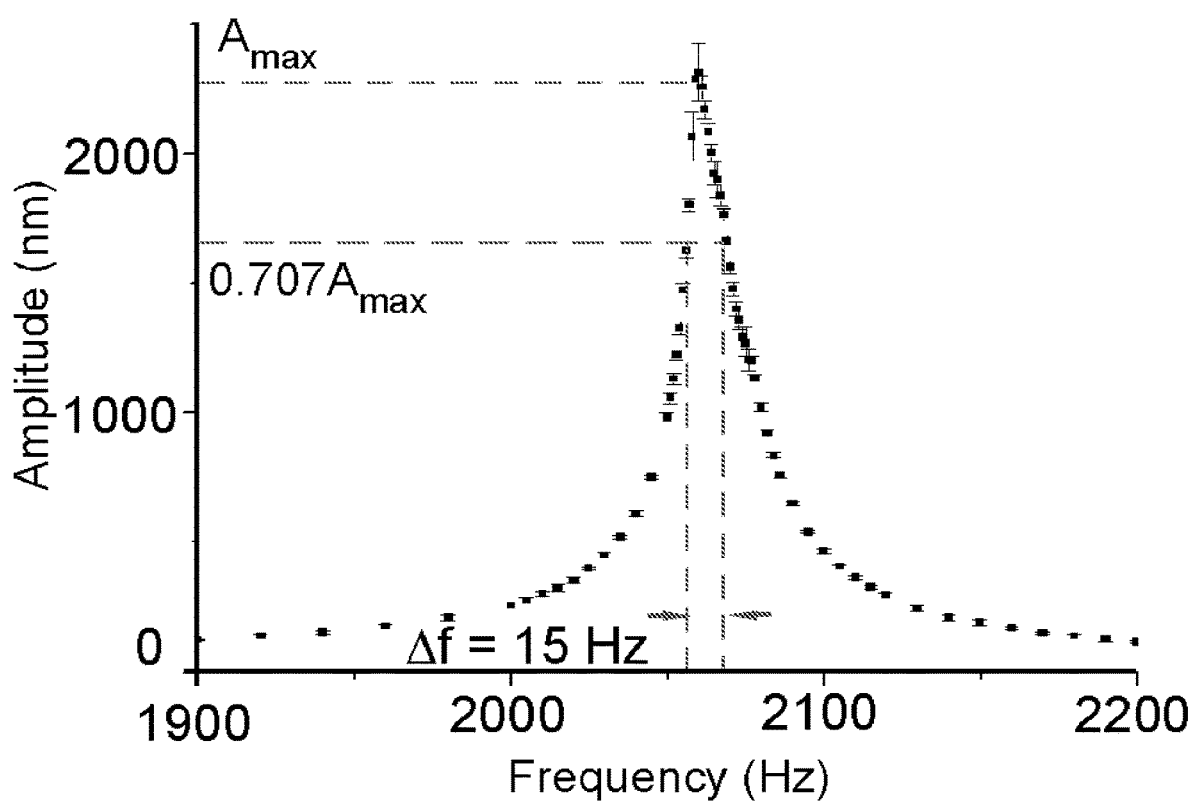
FIGS. 11A and 11B are graphs illustrating the frequency responses of the implantable actuation device illustrated in FIGS. 3A-3E under various testing conditions.
Figure 11B:
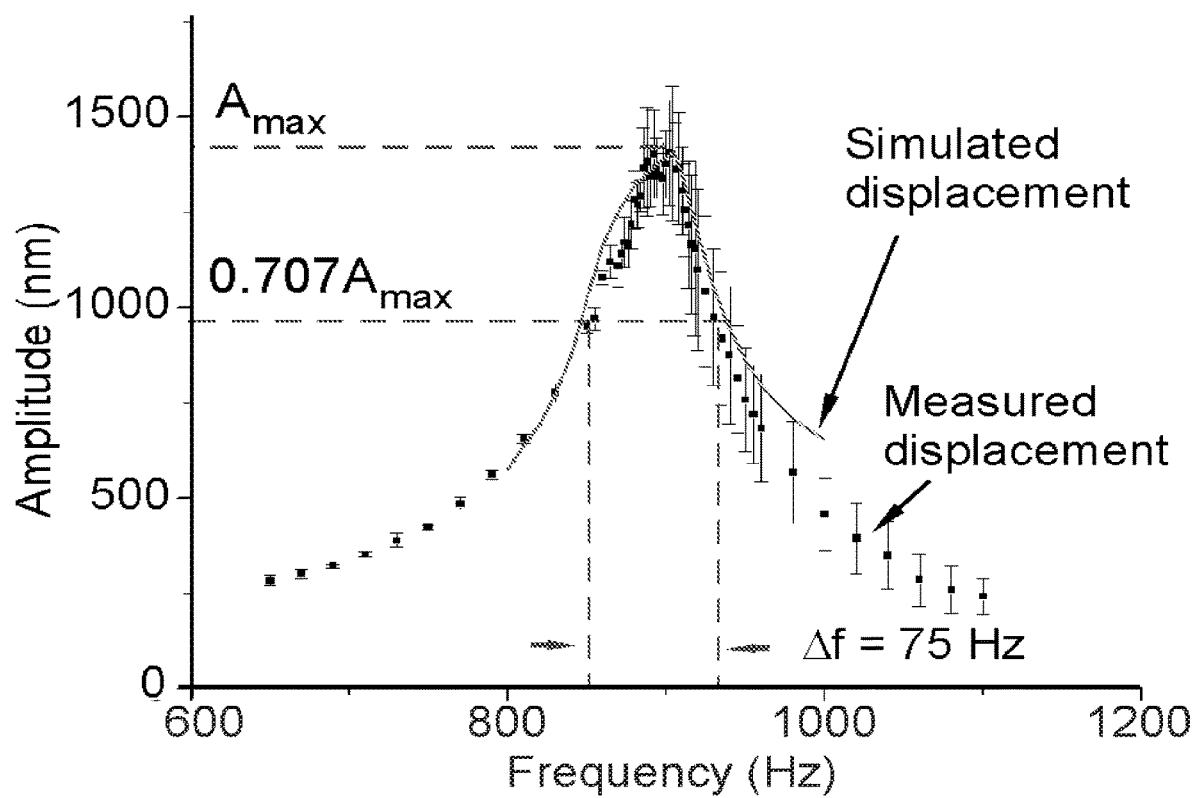

FIGS. 11A and 11B show the frequency response for the implantable actuation device 10 illustrated in FIGS. 3A-3E. FIG. 11A shows the measured frequency response in air measured with a laser displacement meter, and FIG. 11B shows the measured frequency response in water measured with a laser displacement meter. In both experiments, the plotted amplitudes were measured at the center of the actuating paddle 14. A laser displacement sensor such as Model LK-G32 available from the Keyence Corporation of Osaka, Japan may be used to measure the vibration amplitudes. The quality factor of the resonance in air and water may be determined from the frequency response plots shown in FIGS. 11A and 11B. The quality factor Q is approximately equal to $f_0/\Delta f$, where $f_0$ is the resonant frequency and $\Delta f$ is the 3 dB bandwidth. From FIG. 11A, the quality factor in air is given by, $$Q_{air} \approx \frac{f_0}{\Delta f} = \frac{2060}{15} = 137 \quad (3)$$

Similarly, from FIG. 11B, the quality factor in water is given by, $$Q_{water} \approx \frac{f_0}{\Delta f} = \frac{900}{75} = 12 \quad (4)$$

The quality factor in water, $Q_{water}$, can be written as the following equation of its constituent parts:

$$\frac{1}{Q_{water}} = \frac{1}{Q_{int}} + \frac{1}{Q_{visc}} \quad (5)$$

where $Q_{int}$ is the intrinsic loss comprising possible material losses and anchor losses; and $Q_{visc}$ is the loss due to viscous damping in water. Ignoring viscous losses in air, by assuming that intrinsic losses dominate in air, $Q_{air}$ is approximately equal to $Q_{int}$. Hence, from equation (5), $Q_{visc}$ is approximately equal to 13.

The experimentally determined resonance quality factors and frequency response plots of FIGS. 11A and 11B were used to model the damping in the custom coupled magnetomechanical simulation built in COMSOL Multiphysics. The frequency response as simulated by COMSOL is shown in FIG. 11B, superimposed on the measured response. The simulated average magnetic energy, $E_{mag}$, delivered to the resonator by the excitation coils is $2.9 \times 10^{-10}$ J in this particular example. The simulated mechanical energy, $E_{mech}$ of the resonator is $3 \times 10^{-12}$ J. The energy transfer per cycle to the liquid, $E_{liquid}$, through viscous damping, may be $E_{mech}/Q_{visc}$ and is equal to $2.3 \times 10^{-13}$ J in this example. Finally, the conversion efficiency for energy transfer from input magnetic field to the liquid is estimated to be $E_{liquid}/E_{mag}$, or 0.08%.

The results in water for the implantable actuation device 10 illustrated in FIGS. 3A-E in water indicate vibration amplitudes exceeding 1 μm. If these results are extrapolated to other designs using particle velocity measurement results, it may be assumed that vibration amplitudes on the order of hundreds of nanometers can occur across all fabricated actuators illustrated herein. Vibration amplitudes of this order have been previously shown to reduce cellular adhesion. Hence, it can be concluded that the implantable actuation devices illustrated and described herein show sufficient vibration amplitudes to impact cell adhesion and proliferation which can ultimately result in improvement in the effectiveness of the AGDD at lowering IOP and preventing vision loss from glaucoma. Parameters such as amplitude, duration, and periodicity could influence the efficacy of the device and treatment technique, and accordingly, these parameters should be evaluated by a skilled artisan when making or using an implantable actuation device.

Figure 4A:
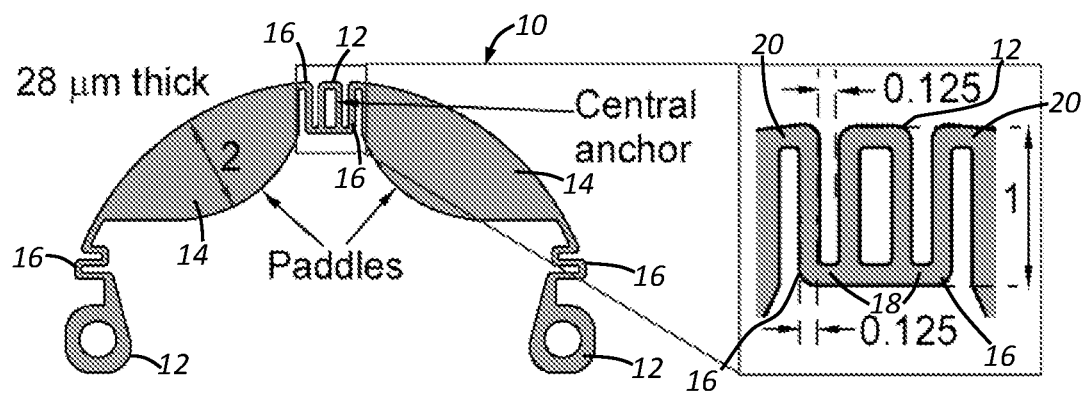
FIGS. 4A-4D illustrate an implantable actuation device according to another embodiment.
Figure 4B:
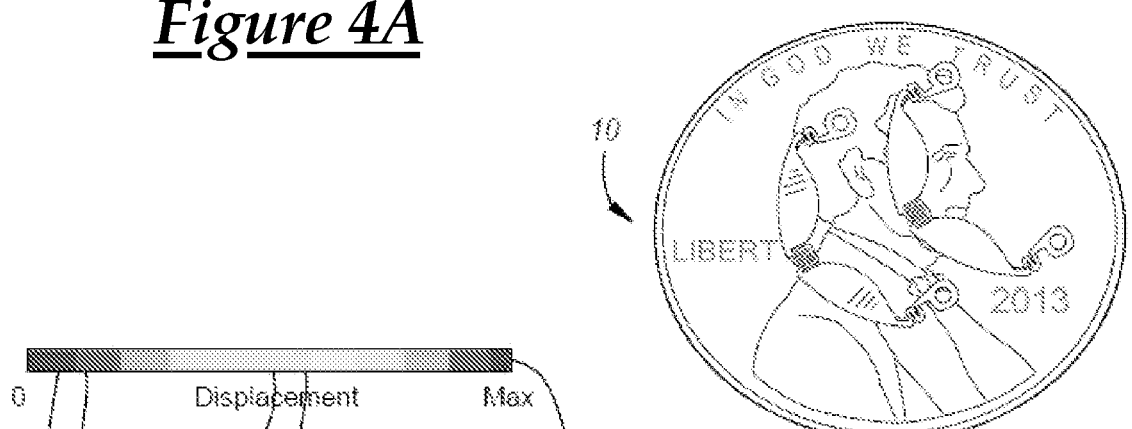
Figure 4C:
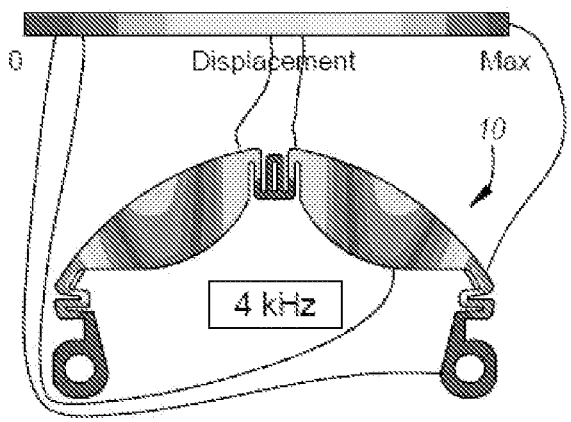
Figure 4D:
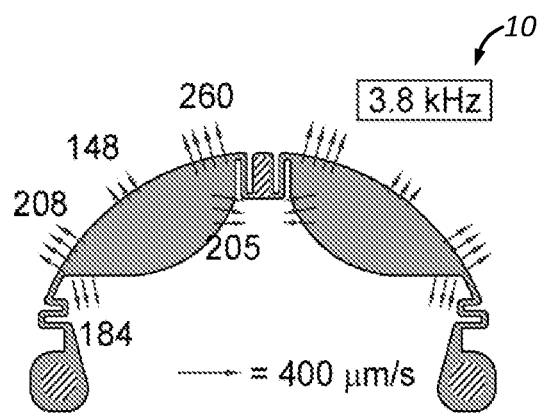

FIGS. 4A-D illustrate another embodiment of an implantable actuation device 10, which may provide increased coverage over a surface. In this embodiment, as well as subsequently disclosed embodiments, reference numerals may be omitted from the corresponding figures for purposes of brevity, but the description of each embodiment and corresponding figure generally follows that of the embodiment disclosed in FIGS. 3A-D except for the differences noted herein, generally. The embodiment illustrated in FIGS. 4A-D includes a central anchor 12 is disposed between two actuating paddles 14. The central anchor may be provided for added security during implantation, such as when a GDD is pushed underneath the conjunctiva with forceps. The central anchor 12 in this specific example measures 1.3×1 mm² and includes beam elements as suspension components 16 that are 125 μm. The actuating paddles 14 measure approximately 2 mm wide at the widest point in this example. The dimensions of the implantable actuation device illustrated in FIGS. 4A-D are approximately 10.3×5.6 mm². FIG. 4C depicts the resonant frequency and mode shape showing maximum resonant amplitudes. In this embodiment, resonant frequencies with large displacements occurred at 4 kHz. In FIG. 4D, estimated particle velocities were observed and schematically represented as with FIG. 3D. This embodiment has five regions where particle flow is generated on each actuating paddle, with an average flow velocity of 200 μm/s at a resonant frequency of 3.8 kHz.

Figure 5A:
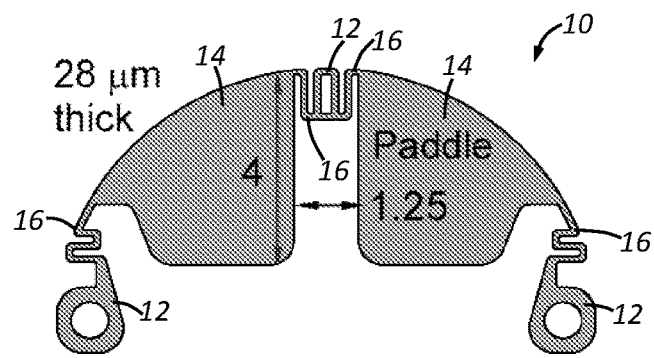
FIGS. 5A-5D depict an implantable actuation device according to another embodiment.
Figure 5B:
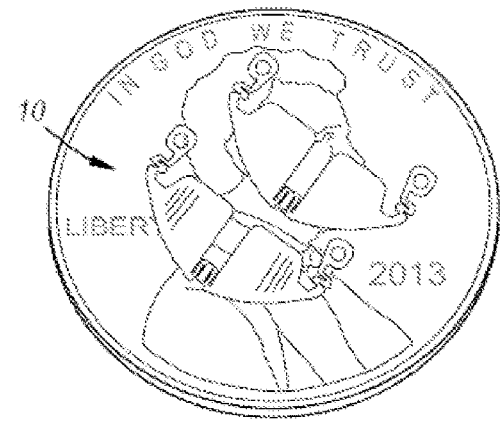
Figure 5C:
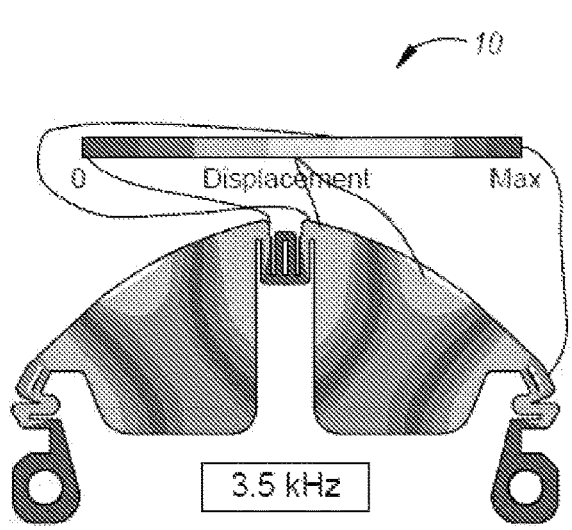
Figure 5D:
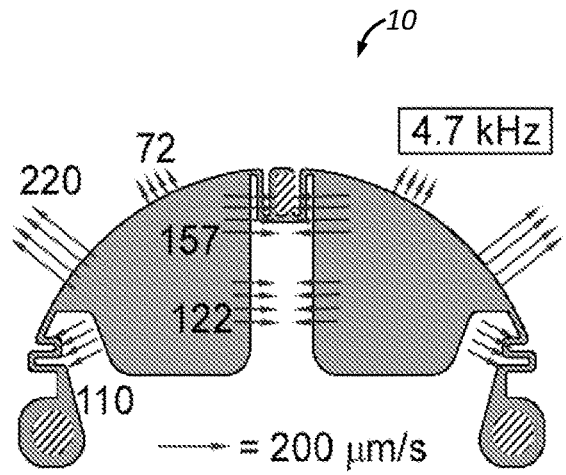

FIGS. 5A-D illustrate another embodiment of an implantable actuation device 10. Similar to FIGS. 4A-D, this design may provide increased coverage over a surface, and includes a central anchor 12 disposed between two actuating paddles 14. The actuating paddles 14 measure approximately 4 mm wide at the widest point in this example. The dimensions of the implantable actuation device illustrated in FIGS. 5A-D are approximately 10.3×5.6 mm², similar to the embodiment illustrated in FIGS. 4A-D. FIG. 5C depicts the resonant frequency and mode shape showing maximum resonant amplitudes. In this embodiment, resonant frequencies with large displacements occurred at 3.5 kHz. In FIG. 5D, estimated particle velocities were observed and schematically represented as with FIG. 3D. This embodiment has five regions where particle flow is generated on each actuating paddle, with an average flow velocity of 135 μm/s at a resonant frequency of 4.7 kHz.

Figure 6A:
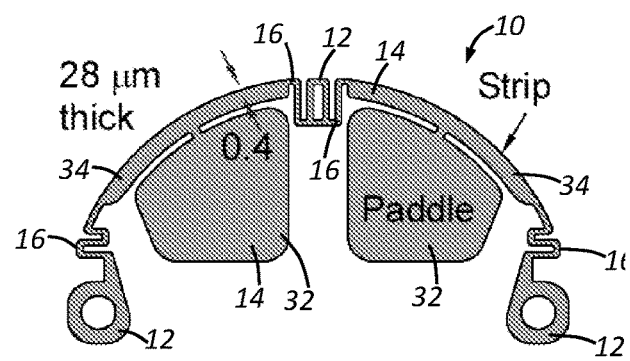
FIGS. 6A-6D show an implantable actuation device according to another embodiment.
Figure 6B:
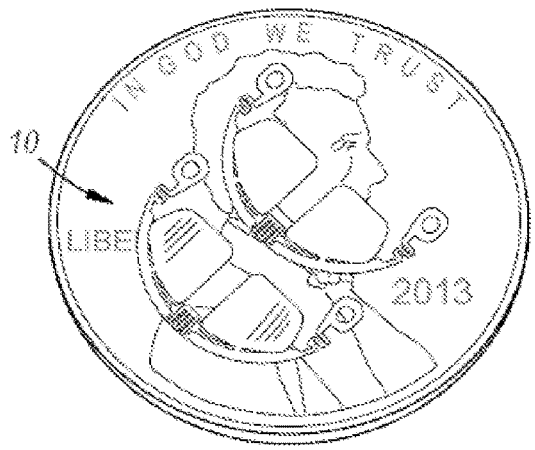
Figure 6C:
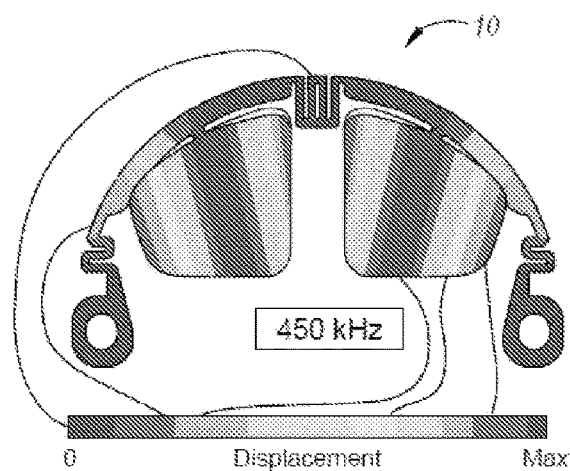
Figure 6D:
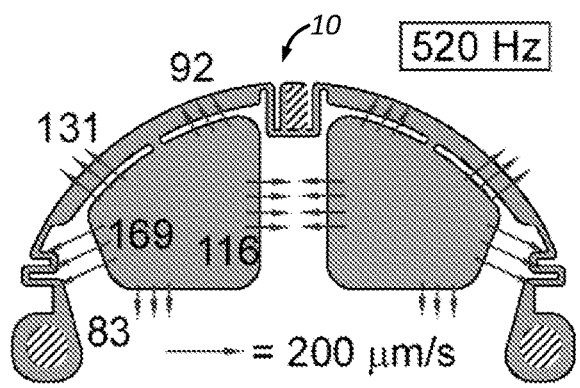

FIGS. 6A-D illustrate another embodiment of an implantable actuation device 10. In this embodiment, each actuating paddle 14 includes a panel portion 32 and a strip portion 34. By dividing each actuating paddle 14 into a panel portion 32 and a strip portion 34, the vibratory motion of the actuating paddles may be increased. In this particular example, the outer radius of the strip portion 34 is 5.1 mm and the inner radius is 4.7 mm, making the strip portion approximately 0.4 mm wide. The panel portions 32 measure approximately 3.25 mm at their widest point. The entire actuator in this example measures 10.3×5.6 mm². FIG. 6C depicts the resonant frequency and mode shape showing maximum resonant amplitudes. In this embodiment, resonant frequencies with large displacements occurred at 450 Hz, which is lower than other embodiments. In FIG. 6D, estimated particle velocities were observed and schematically represented as with FIG. 3D. This embodiment has five regions where particle flow is generated on each actuating paddle, with an average flow velocity of 118 μm/s at a resonant frequency of 520 Hz.

Figure 7A:
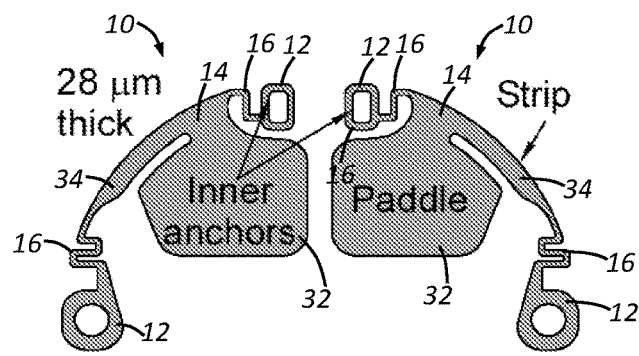
FIGS. 7A-7D illustrate an embodiment that includes two implantable actuation devices.
Figure 7B:
Figure 7C:
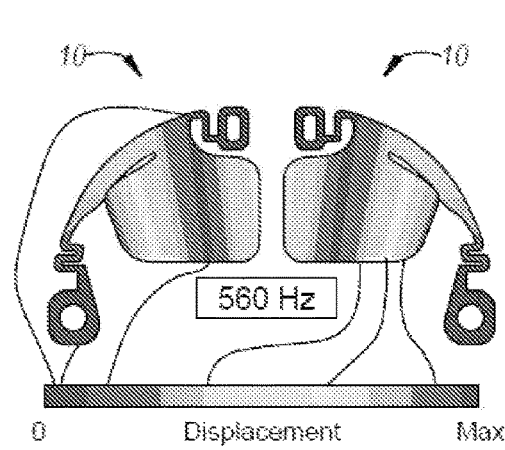
Figure 7D:
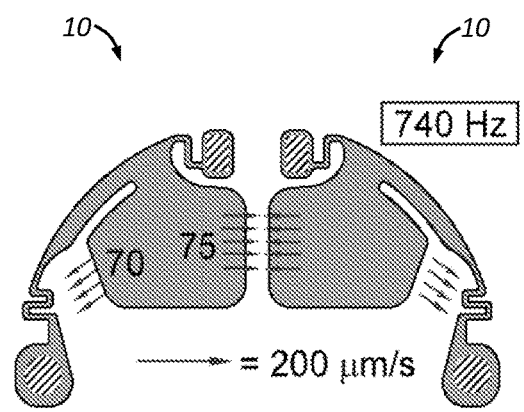

FIGS. 7A-D illustrate another embodiment, where two implantable actuation devices 10 may be used, such as by attaching them to a GDD. Including two implantable actuation devices may help to accommodate deformations in soft GDD plate surface shapes, for example. Each actuating paddle 14 may include a panel portion 32 attached to a strip portion 34 that may circumscribe a portion of the surface of a GDD, with one end of the strip portion being attached to an outer suspension component and anchor, and the other end to another suspension component and anchor. The outer radius of the strip portion 34 is 5.1 mm and the inner radius is 4.7 mm, making the strip portion approximately 0.4 mm wide. The inner anchors 12 measure approximately 1×0.7 mm² and the inner suspension components 16 measure 0.7×0.6 mm², and in this embodiment, are made from beam elements that are 125 μm wide. This embodiment includes attachment of the panel portion 32 and strip portion 34 towards the end of the strip portion, thereby resulting in a flexural motion of the strip portion 34 and a torsional motion of the panel portion 32. FIG. 7C depicts the resonant frequency and mode shape showing maximum resonant amplitudes. In this embodiment, resonant frequencies with large displacements occurred at 560 Hz. In FIG. 7D, estimated particle velocities were observed and schematically represented as with FIG. 3D. This embodiment has two regions where particle flow is generated on each actuating paddle, with an average flow velocity of 73 μm/s at a resonant frequency of 740 Hz.

Figure 8A:
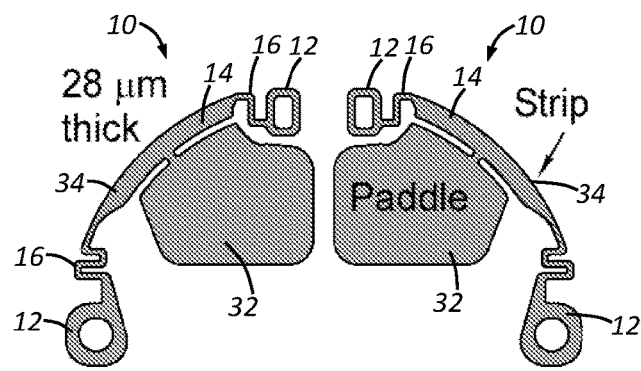
FIGS. 8A-8D depict another embodiment that includes two implantable actuation devices.
Figure 8B:
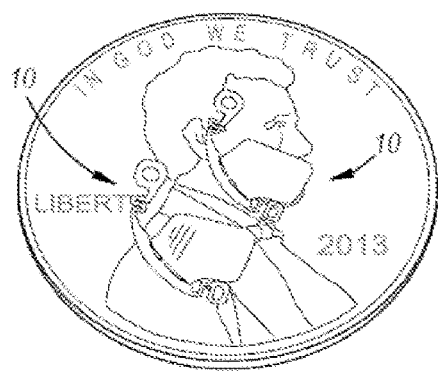
Figure 8C:
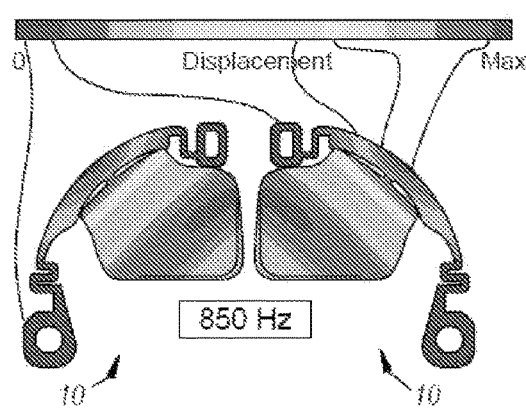
Figure 8D:
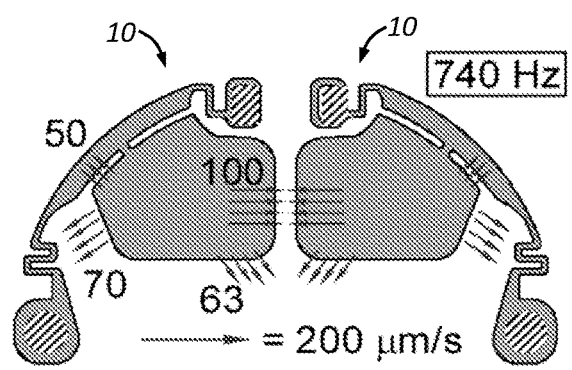

FIGS. 8A-D illustrate another embodiment, similar to that illustrated in FIGS. 7A-D, where two implantable actuation devices 10 may be used, such as by attaching them to a GDD. Each actuating paddle 14 may include a panel portion 32 attached to a strip portion 34 that may circumscribe a portion of the surface of a GDD, with one end of the strip portion being attached to an outer suspension component and anchor, and the other end to another suspension component and anchor. The dimensions may be similar to those disclosed with relation to the embodiment illustrated in FIGS. 7A-D; however, unlike the embodiment illustrated in FIGS. 7A-D, this embodiment has a central attachment between the panel portion 32 and the strip portion 34 of the actuating panel 34. This particular arrangement may result in a flexural motion of the strip portion 34 and a transverse motion in the panel portion 32. FIG. 8C depicts the resonant frequency and mode shape showing maximum resonant amplitudes. In this embodiment, resonant frequencies with large displacements occurred at 850 Hz. In FIG. 8D, estimated particle velocities were observed and schematically represented as with FIG. 3D. This embodiment has four regions where particle flow is generated on each actuating paddle, with an average flow velocity of 70 µm/s at a resonant frequency of 740 Hz.

A method of fabricating an implantable ocular actuation device, such as the implantable actuation device 10 depicted in the figures, may include the steps of patterning a thin film magnetoelastic alloy and annealing the thin film so that it is shaped to have a three-dimensional, non-spherically shaped profile with a small form factor. Magnetoelastic materials are typically available in both crystalline and amorphous forms. Of particular interest for microscale sensing and actuation applications are amorphous magnetoelastic alloys that are commercially available as planar foils. Microfabrication techniques like micro-electrodischarge machining (µEDM) and photochemical machining (PCM) can be used to pattern these materials with spatial resolution down to a few tens of micrometers. In contrast to crystalline materials, amorphous magnetoelastic alloys operate at a lower bias field reducing the size of the biasing magnet or electric current that is necessary, which may be beneficial in some embodiments. Moreover, amorphous magnetoelastic materials can be tailored to have high magnetomechanical coupling coefficients (i.e., conversion efficiency between magnetic and mechanical energy), through the process of annealing in the presence of a magnetic field, thereby providing a stronger resonant response for a given stimulus.

In a preferred embodiment, implantable actuation devices are fabricated from 29 µm-thick foil of Metglas 2826 MB ($Fe_{40}Ni_{38}Mo_4B_{18}$) (Metglas, Inc., Conway, S.C.). It has a saturation magnetostriction of 12 ppm and a DC permeability greater than 50000. The high permeability can be beneficial in attracting and directing the biasing magnetic field along the actuator, allowing some leeway in the alignment of the DC magnetic field coils.

As previously mentioned, fabrication of the actuators can be a two-step process: patterning of the thin-film magnetoelastic alloy, followed by thermal annealing to induce the desired curvature. The implantable actuation devices may be patterned from the flat sheets of Metglas 2826 MB using PCM (Kemac Technology, Inc., Azusa, Calif.). In this process, the foil may first be coated with a photoresist which is lithographically patterned by ultraviolet exposure. The exposed regions of the substrate (not covered by the mask) can then be etched away using a spray of etchant. Advantages of this technique include burr-free fabrication and retention of magnetic properties. In the second step, to obtain the necessary curvature on the actuator, the patterned sheet of Metglas 2826 MB should be annealed at elevated temperatures in a mold to remove the stress induced by the applied curvature. A longer annealing duration or higher temperature can the initially flat structure to conform to the curvature of anneal molds to a higher degree. A potential downside is that higher temperature annealing can result in embrittlement. Furthermore, a temperature that is too high can also lead to crystallization of the material or loss of ferromagnetism if it exceeds the Curie point, thereby resulting in a reduction in permeability. The Curie temperature for Metglas 2826 MB is 353° C. and the temperature of crystallization is 440° C. Conversely, shorter annealing duration times or the use of a lower annealing temperature may prevent the shape of the mold from being completely transferred to the finished implantable actuation device. Preliminary experiments directed to inducing curvature on the actuation devices indicated that the recoil is usually 25-40% of the target deformation when removed from mold. The shape of the mold should account for this partial recoil. In one specific example, annealing at 275° C. for 12 hours in a mold with exaggerated curvature provides an operable device having a small form factor and a three-dimensional, non-spherically shaped profile.

Figure 12:
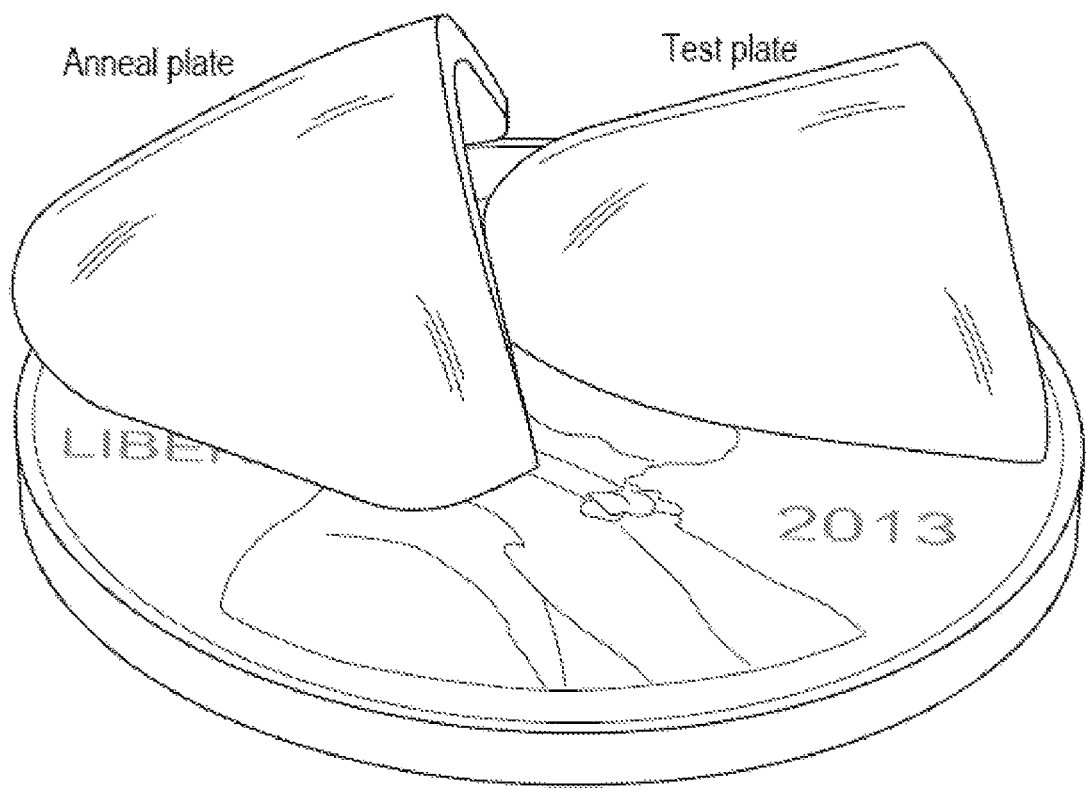
FIG. 12 is a photo of embodiments of fabrication plates that may be used to anneal an implantable actuation device.

As illustrated in FIG. 12, an anneal mold can consist of two plates with exaggerated curvatures. In one example, a photochemically machined sheet of Metglas 2826 MB may be sandwiched between the two plates during the annealing process. The plates in the illustrated embodiment were designed using the three-dimensional scanned model of the GDD 24 described above and fabricated using direct metal laser sintering (DMLS) with a cobalt-chrome alloy (GPI Prototype and Manufacturing Services, Lake Bluff, Ill.). In the DMLS process, which is an additive manufacturing process, a laser may be used to sinter powdered metal, layer-by-layer, to create the required solid structure. In addition to the plates used for annealing, DMLS was also used for fabricating test plates that mimic the curvature of the GDD. During experimental measurements, the implantable actuation devices were attached to the illustrated test plates to replicate the curvature of the GDD. The fabrication method may also include the step of coating the thin film with a biocompatible material, such as a 1 µm layer of Parylene-C to prevent corrosion.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. An implantable actuation device, comprising:
    an anchor adapted for fixedly mounting the implantable actuation device to a non-planar surface;
    an actuating paddle comprised of a magnetoelastic material, wherein the actuating paddle has a non-spherical shape having at least one bend or curve within a plane of the actuating panel and at least one bend or curve out of the plane of the actuating panel, wherein the actuating paddle is configured to conformally rest near the non-planar surface; and a suspension component having a first end attached to the anchor and a second end attached to the actuating paddle, wherein the suspension component allows for relative movement between the fixedly mounted anchor and the actuating paddle when the implantable actuation device is mounted to the non-planar surface.

2. The implantable actuation device of claim 1, wherein the non-planar surface is an ocular surface.

3. The implantable actuation device of claim 1, wherein the actuating paddle includes a panel portion and a strip portion.

4. The implantable actuation device of claim 1, comprising a plurality of anchors and a plurality of suspension components.

5. The implantable actuation device of claim 4, comprising a plurality of actuating paddles.

6. The implantable actuation device of claim 5, wherein two actuating paddles are connected via a central anchor.

7. The implantable actuation device of claim 4, wherein the actuating paddle extends between two anchors attached via two suspension components.

8. A glaucoma drainage device, comprising:
the implantable actuation device of claim 1;
a body having the non-planar surface; and
a drainage tube attached to the body,
wherein the anchor of the implantable actuation device is fixedly mounted to the non-planar surface of the body of the glaucoma drainage device.

9. The glaucoma drainage device of claim 8, comprising a plurality of actuation devices.

10. An implantable ocular actuation device, comprising:
a magnetoelastic membrane having a non-spherical shape having at least one bend or curve within a plane of an actuating panel and at least one bend or curve out of the plane of the actuating panel, wherein at least one side of the magnetoelastic membrane has an arcuate shape.

11. A glaucoma drainage device comprising the implantable ocular actuation device of claim 10.

12. A method of fabricating an implantable ocular actuation device comprising the steps of:

patterning a magnetoelastic alloy membrane; and
annealing the membrane to shape it so that the membrane has a non-spherical shape having at least one bend or curve within a plane of an actuating panel and at least one bend or curve out of the plane of the actuating panel, wherein at least one side of the membrane has an arcuate shape.

13. The method of claim 12, further comprising the step of coating the membrane with a biocompatible material.

14. A method of preventing cell adhesion resulting from a glaucoma treatment procedure, comprising the steps of:
anchoring a magnetoelastic paddle actuator to a non-planar ocular surface or a non-planar surface of a glaucoma drainage device, wherein the magnetoelastic paddle actuator has a a non-spherical shape having at least one bend or curve within a plane of the magnetoelastic paddle actuator and at least one bend or curve out of the plane of the magnetoelastic paddle actuator, wherein the magnetoelastic paddle actuator is configured to conformally rest near the non-planar ocular surface or the non-planar surface of the glaucoma drainage device; and
wirelessly applying a magnetic field to the magnetoelastic paddle actuator so that the paddle actuator vibrates and dispels at least some fibroblasts from the paddle actuator itself, the ocular surface, and/or the surface of the glaucoma drainage device.

15. The method of claim 14, wherein vibratory motion of the magnetoelastic paddle actuator is out of the plane defined by the magnetoelastic paddle actuator.

16. An actuation device, comprising:
an anchor adapted for fixedly mounting the actuation device to a surface;
an actuating paddle comprised of a magnetoelastic material; and
a spring suspension component comprised of the magnetoelastic material, the spring suspension component having a first end attached to the anchor and a second end attached to the actuating paddle, wherein the spring suspension component allows for relative movement between the fixedly mounted anchor and the actuating paddle when the actuation device is mounted to the surface.

* * * * *